(12) United States Patent
Howes

(10) Patent No.: US 10,343,044 B2
(45) Date of Patent: Jul. 9, 2019

(54) METHOD AND APPARATUS FOR SCORING SHOOTING EVENTS USING HEARING PROTECTION DEVICES

(71) Applicant: Starkey Laboratories, Inc., Eden Prairie, MN (US)

(72) Inventor: Christopher Larry Howes, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 414 days.

(21) Appl. No.: 14/802,546

(22) Filed: Jul. 17, 2015

(65) Prior Publication Data

US 2016/0076858 A1 Mar. 17, 2016

Related U.S. Application Data

(60) Provisional application No. 62/051,140, filed on Sep. 16, 2014.

(51) Int. Cl.
| | |
|---|---|
| *F41J 5/06* | (2006.01) |
| *A61F 11/06* | (2006.01) |
| *A63B 71/06* | (2006.01) |
| *F41A 19/01* | (2006.01) |

(52) U.S. Cl.
CPC .............. *A63B 71/06* (2013.01); *A61F 11/06* (2013.01); *F41A 19/01* (2013.01); *F41J 5/06* (2013.01)

(58) Field of Classification Search
CPC ...... A63B 71/0669; A63B 71/06; H04R 3/00; A61F 11/06; F41A 19/01; F41J 5/06
See application file for complete search history.

(56) References Cited

U.S. PATENT DOCUMENTS

| | | | |
|---|---|---|---|
| 3,680,863 A * | 8/1972 | Wallace | F41J 11/00 124/32 |
| 7,266,045 B2 | 9/2007 | Baxter | |
| 8,730,062 B2 | 5/2014 | Eldershaw et al. | |
| 2006/0044140 A1* | 3/2006 | Berg | A61F 11/08 340/573.1 |
| 2008/0240458 A1* | 10/2008 | Goldstein | H04R 25/453 381/72 |

(Continued)

FOREIGN PATENT DOCUMENTS

DE 202013008543 U1 3/2014

OTHER PUBLICATIONS

"European Application Serial No. 15185174.8, Extended European Search Report dated Feb. 9, 2016", 7 pgs.

*Primary Examiner* — Xuan M Thai
*Assistant Examiner* — Malina D. Blaise
(74) *Attorney, Agent, or Firm* — Schwegman Lundberg & Woessner, P.A.

(57) ABSTRACT

A system for scoring a shooting event for a shooter includes a pair of hearing protection devices and a portable device. The hearing protection devices each include an electronic circuit that detects a gunshot and produces detection information characterizing the gunshot as detected. The difference between the detection information produced by the hearing protection devices worn in or over different ears of the shooter allows the portable devices to identify the gunshot as being fired by the shooter and subsequently prompt the shooter to give a voice command indicating the result of the gunshot to the portable device for the scoring without manual entry.

21 Claims, 5 Drawing Sheets

(56) References Cited

U.S. PATENT DOCUMENTS

| | | | |
|---|---|---|---|
| 2010/0215198 A1* | 8/2010 | Ngia | H04R 1/1016 381/309 |
| 2012/0177217 A1* | 7/2012 | Schmidt | H04L 1/0001 381/80 |
| 2013/0064378 A1 | 3/2013 | Chuang | |
| 2013/0139600 A1* | 6/2013 | McEwen-King | G01H 9/004 73/655 |
| 2013/0193645 A1* | 8/2013 | Kazakov | F41J 5/06 273/372 |
| 2013/0202120 A1* | 8/2013 | Bickel | G08B 13/1672 381/56 |
| 2013/0278631 A1* | 10/2013 | Border | G02B 27/017 345/633 |
| 2015/0023591 A1* | 1/2015 | Potluri | F41J 5/10 382/162 |
| 2015/0162047 A1* | 6/2015 | Lacirignola | G10L 21/0208 700/94 |
| 2016/0030829 A1* | 2/2016 | Rowsey | A63B 71/0669 340/323 R |

\* cited by examiner

METHOD AND APPARATUS FOR SCORING SHOOTING EVENTS USING HEARING PROTECTION DEVICES

CLAIM OF PRIORITY

The present application claims the benefit of priority under 35 U.S.C. § 119(e) of U.S. Provisional Patent Application Ser. No. 62/051,140, filed on Sep. 16, 2014, which application is incorporated herein by reference in its entirety.

TECHNICAL FIELD

This document relates generally to audio systems and more particularly to a wireless system using hearing protection devices and a mobile device for scoring shooting events.

BACKGROUND

Scoring tools currently used in recreational and competitive shooting events include paper based scoring charts and electronic scoring devices that require manual input. During a shooting event, scores need to be manually entered either during or after a round of shooting. Competitive shooting requires concentration for good performance. When the shooter makes manual scoring entries during either practice or a competition, the distraction is tedious and breaks the rhythm of the shooter who needs to fully concentrate on the targets. Trying to memorize scores to enter after the round of shootings may be similarly distractive for the shooter. Thus, scoring a shooting event with such tools either depends on help of another person or distracts the shooter during a round of shootings in a shooting event.

SUMMARY

A system for scoring a shooting event for a shooter includes a pair of hearing protection devices and a portable device. The hearing protection devices each include an electronic circuit that detects a gunshot and produces detection information characterizing the gunshot as detected. The difference between the detection information produced by the hearing protection devices worn in or over different ears of the shooter allows the portable devices to identify the gunshot as being fired by the shooter and subsequently prompt the shooter to give a voice command indicating the result of the gunshot to the portable device for the scoring without manual entry.

In one embodiment, the system includes a pair of hearing protection devices configured to protect hearing of the shooter from injurious sounds and a portable device. The pair of hearing protection devices includes a first ear device configured to be worn in or over one ear of the shooter and a second ear device configured to be worn in or over the other ear of the shooter. The first ear device detects a gunshot and produces first detection information characterizing the gunshot as detected by the first ear device. The second ear device detects the gunshot and produces second detection information characterizing the gunshot as detected by the second ear device. The portable device is communicatively coupled to the pair of hearing protection devices via a wireless link, and detects an acoustic signature using the first detection information and the second detection information. The acoustic signature allows for identification of the gunshot as being fired by the shooter. In one embodiment, the portable device receives a voice command from the shooter following the identification of the acoustic signature, and scores the gunshot according to the voice command.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1:
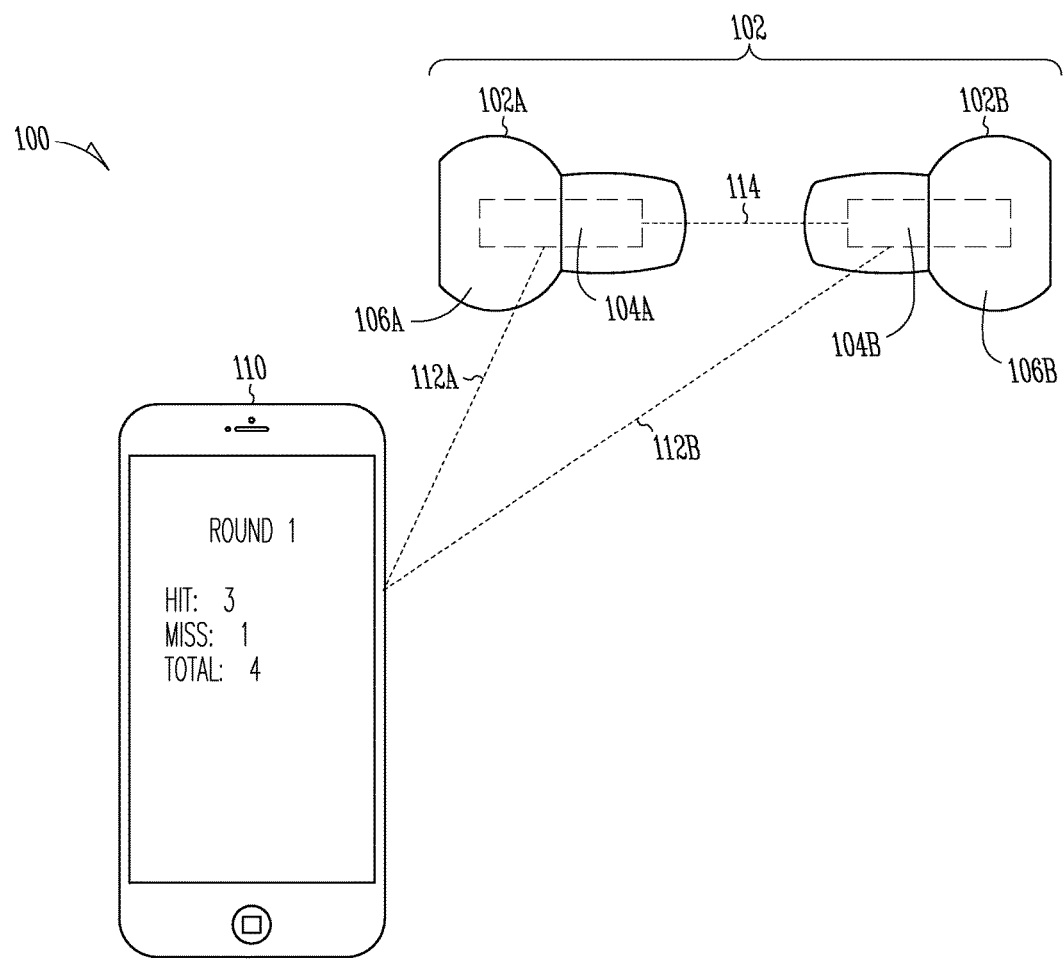
FIG. 1 is a block diagram illustrating an embodiment of a system for scoring a shooting event using a pair of hearing protection devices and a portable device.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses, among other things, a system for shooting scoring using hearing protection devices and a portable device. Current tools for scoring shooting events include paper based and electronics based charts that require manual input to track the scores during a round of shootings in a recreational or competitive shooting event such as clay pigeon shooting. This distracts the shooter from concentrating on the targets. The present system is configured to characterize a gunshot fired by a specific shooter using a pair of hearing protection devices worn by that shooter and a portable device communicatively coupled to the pair of hearing protection devices. When the gunshot is recognized as being fired by the shooter, the system prompts the shooter to give a verbal command indicating a result of the gunshot, such as by saying "hit" or "miss". Thus, the present system tracks the scoring without requiring manual interaction with the shooter. In various embodiments, the hearing protection system includes audio electronics integrated into the pair of hearing protection devices that protects the shooter's ears from the loud noise of the gunshots, and the portable device may include a mobile device.

Unless noted otherwise, "a shooter" or "the shooter" in this document refers to the specific individual shooter using the present system as implemented in a specific set of hearing protection devices and portable device. The shooter is the wearer of hearing protection devices and the user of the portable device. Discussions of the present system in this document assume a single system including the specific set of hearing protection devices and portable device used by the specific individual shooter. Other shooters are each referred to as "another shooter" or "the other shooter". One or more of the other shooters may use the present system as implemented in another specific set of hearing protection devices and portable device.

In one embodiment, the pair of hearing protection devices includes a pair of wireless earbuds, and the portable device includes a smartphone. The wireless earbuds include external microphones to be used to keep the wearer (i.e., the shooter) in touch with the environment while still providing a similar noise reduction rating that is currently gained from a more traditional hearing protection device. The wireless earbuds communicate with the smartphone via a wireless communication link such as a Bluetooth or Bluetooth Low Energy (BLE) link. The smartphone includes a mobile application that allows the wearer of the hearing protection devices to control the volume of the external microphones and any streamed audio signals, and customize the response of the external microphones and save the customized settings for unique environments. In various embodiments, the mobile application may include the ability to track scoring for traditional clay pigeon shooting events such as trap shooting, skeet shooting, and sporting clays, as well as other shooting sports such as biathlon and 3-gun shooting. Instead of tracking the score through manual entry while trying to concentrate on the shooting, the present system allows the shooter, who wears the wireless earbuds, to track the score using a voice commend following each gunshot.

In various embodiments, when the shooter is engaged with the mobile application and is wearing the wireless earbuds in both left and right ears and has the wireless earbuds communicatively coupled to the smartphone, the mobile application can be calibrated to an acoustic signature allowed the gunshot to be identified as being fired by the shooter. The scoring process for a shooting event starts with the calibration, for which the smartphone prompts the shooter to fire one or more test gunshots from his or her normal shooting position. The wireless earbuds detect the sound level (such as measured by decibel level, or dB level) associated with each ear of the shooter using their microphones, and may also measure the time of the peak of the sound level associated with each ear. Such sound level and/or timing information are then transmitted to the smartphone, where the mobile application creates the acoustic signature using the sound level and/or timing information. This acoustic signature is unique to the shooter shooting the one or more test gunshots during the calibration and dependent on how the shooter shoulders the gun, and is saved by the mobile application for recognizing only the gunshots fired by the shooter while ignoring gunshots by another shooter or other shooters, if present. Following the calibration, the shooter can start shooting for scoring and track the score by voice commands. When turned on, the mobile application monitors for the acoustic signature associated with the shooter. Whenever a gunshot fired by the shooter is recognized using the acoustic signature, the smartphone delivers a tone to the shooter, directly or through one or both of the wireless earbuds. The shooter is then given some amount of time to speak a command, such as "hit" or "miss", to be received by the smartphone, directly or through one or both of the wireless earbuds. The command is interpreted by the mobile application for use to score the gunshot recognized using the acoustic signature. In various embodiments, the mobile application produces tones for the smartphone to deliver to the shooter for each gunshot to be scored to let the shooter know that a voice command is expected for that gunshot.

While the wireless earbuds and smartphone are discussed as a specific example, the hearing protection devices in the present system may include any type of devices that protect the wearer from injurious effects to his or her hearing, and the portable device may include any type of device suitable for being communicatively coupled to the hearing protection devices to perform the scoring process as further discussed below in this document. In various embodiments, the hearing protection devices include a pair of devices worn in or about each of the left and right ears of the wearer/shooter, and the portable device is suitable for bringing to and use in the site where the wearer/shooter fires gunshots in a shooting event.

FIG. 1 is a block diagram illustrating an embodiment of a system 100 for scoring a shooting event using a pair of hearing protection devices and a portable device. System 100 includes a pair of hearing protection devices 102 configured to protect hearing of a shooter from injurious sounds and a portable device configured to wirelessly communicate with the pair of hearing protection devices 102. Hearing protection devices 102 include a first hearing device 102A configured to be worn in or over the first ear of the shooter and a second hearing device 102B configured to be worn in or over the second ear of the shooter. In various embodiments, the first ear is the left ear, and the second ear is the right ear. In various other embodiments, the first ear is the right ear, and the second ear is the left ear. In some embodiments, each of first and second hearing devices 102A-B is not configured to be left or right ear-specific.

First ear device 102A includes a first hearing circuit 104A housed in a first case 106A. First hearing circuit 104A detects a gunshot and produces first detection information characterizing the gunshot as detected by first hearing circuit 104A. Second ear device 102B includes a second hearing circuit 104B housed in a second case 106B. Second hearing circuit 104B detects the same gunshot and produces second detection information characterizing the gunshot as detected by second hearing circuit 104B. The difference between the first detection information and the second detection information allows for recognition of the gunshot as being fired by the shooter, rather than a gunshot fired by another shooter in the vicinity. Cases 106A and 106B are each shaped and made of acoustically insulative material to provide the shooter with protection against sounds that are injurious to his or her hearing functions, including gunshot sounds.

Portable device 110 is configured to be communicatively coupled to the pair of hearing protection devices 102 via a wireless link. In the illustrated embodiment, a wireless communication link 112A allows for communication between first ear device 102A and portable device 110, a wireless communication link 112B allows for communication between second ear device 102B and portable device 110, and a wired or wireless communication link 114 allows for communication between first ear device 102A and second ear device 102B. In various embodiments, system 100 includes at least two of communication links 112A, 112B, and 114. For example, portable device 110A may communicate with first ear device 102A via communication link 112A and with second ear device 102B via communication link 112B, or it may communicate with first ear device 102A via communication link 112A and second ear device 102B via first ear device 102A and communication link 114, or it may communicate with second ear device 102B via communication link 112B and first ear device 102A via second ear device 102B and communication link 114.

Portable device 110 detects an acoustic signature using the first detection information and the second detection information. The acoustic signature allows for identification of the gunshot as being fired by the shooter. In various embodiments, portable device 110 receives a voice command from the shooter following the identification of the gunshot as being fired by the shooter, and scores the gunshot according to the voice command.

Hearing protection devices 102 as illustrated in FIG. 1 are configured as a pair of wireless earbuds. In various embodiments, hearing protection devices 102 may be configured as any type of devices capable of protecting the shooter from injurious sounds including gunshot sounds while housing hearing circuits 104A-B. Examples of hearing protection devices 102 include earbuds, earplugs, earmuffs, headphones, and hearing assistance devices with hearing protective mechanism, such as hearing aids housed in hearing protective cases. In various embodiments, portable device 110 can be any device that is suitable for use by the shooter during shooting events and capable of being configured to perform shooting scoring functions as discussed in this document. Examples of portable device 110 include mobile devices such as a smartphone, a laptop or tablet computer, and a personal digital assistance (PDA) device.

Figure 2:
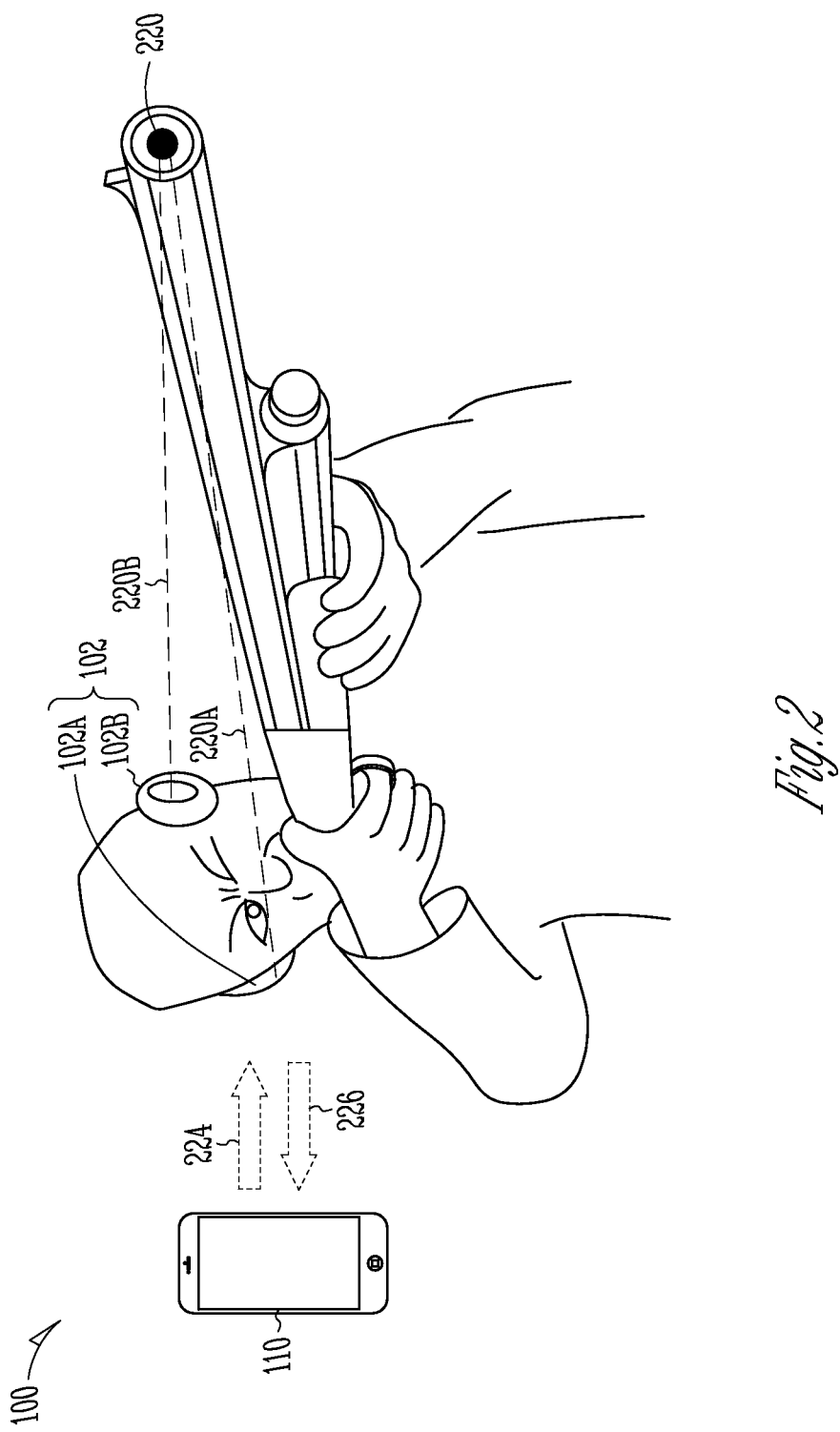
FIG. 2 is an illustration of a concept of operation of the system of FIG. 1.

FIG. 2 is an illustration of a concept of operation of system 100. The shooter wears hearing protection devices 102, including first ear device 102A in or over the right ear and second ear device 102B in or over the left ear. Portable device 110 is carried by the shooter or placed in proximity to the shooter during the shooting event such that communication between hearing protection devices 102 and portable device 110 can be reliably performed. Portable device 110 transmits signals 224 to hearing protection devices 102, such as command prompting the shooter to take certain actions and/or notifying the shooter of the status of scoring. Hearing protection devices 102 transmit signals 226 to portable devices 110, such as information about a gunshot acquired by hearing protection devices 102 and/or voice commands given by the shooter for the operation of portable device 110.

When the shooter fires a gunshot, the sound of the gunshot travels from a gunshot sound source 220 to first ear device 102A (worn over the right ear as shown by way of example) via sound path 222A and second ear device 102B (worn over the left ear as shown by way of example) via sound path 222B. The difference between the lengths of sound path 222A and sound path 222B allows for distinguishing a gunshot fired by the shooter from gunshots fired by other shooters that may also be detected by first and second ear devices 102A-B. One or more parameters resulting from such a difference that is unique to the shooter are used as an acoustic signature for the shooter. In one embodiment, the acoustic signature includes a time delay between the gunshot as detected by first ear device 102A and the same gunshot as detected by second ear device 102B. In another embodiment, the acoustic signature includes a sound level difference between the sound level of the gunshot as detected by first ear device 102A and the sound level of the same gunshot as detected by second ear device 102B. In various embodiments, the sound level is measured by decibels (dB). In various embodiments, the acoustic signature may include the time delay, the sound level difference, and/or other information resulting from the difference between sound paths 222A and 222B, depending on whether each of these parameters is detectable in practice.

Figure 3:
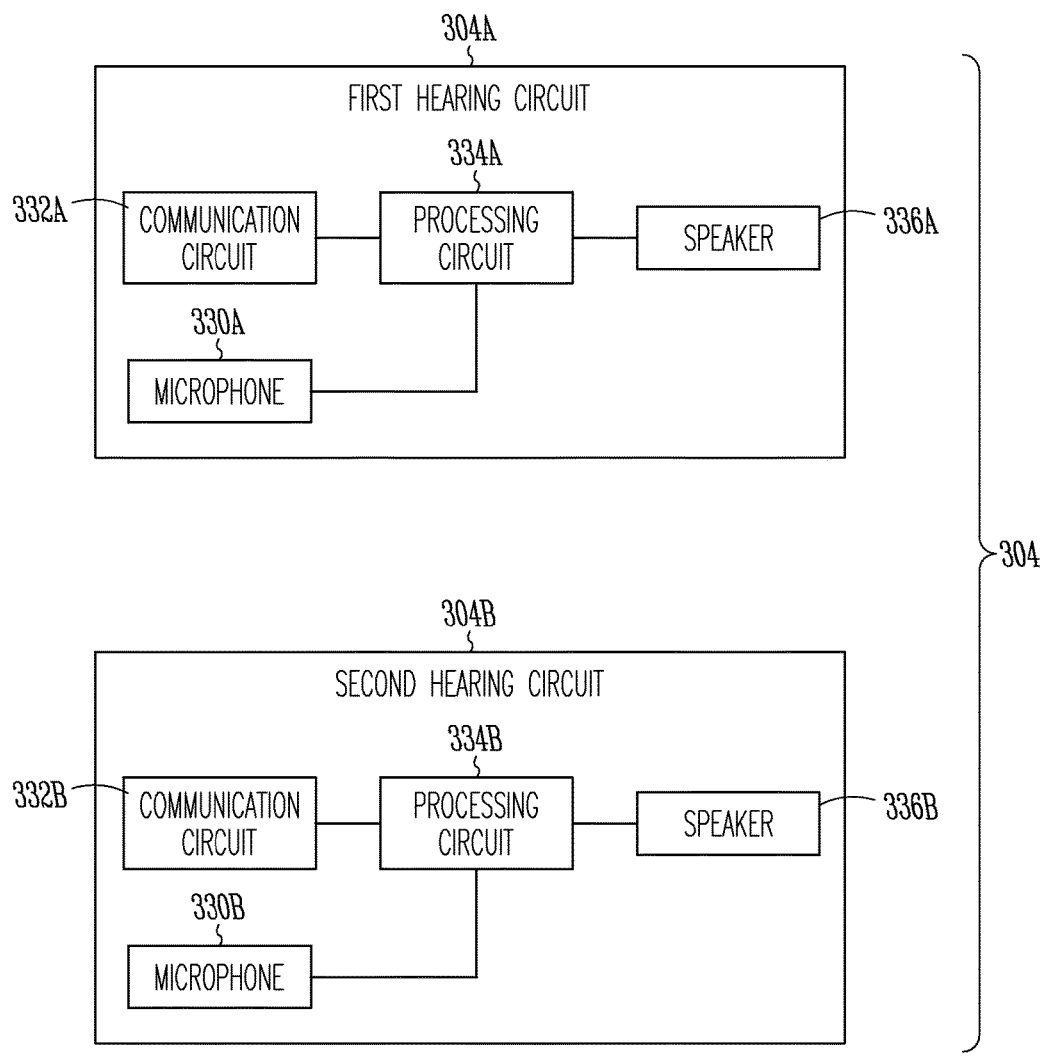
FIG. 3 is a block diagram illustrating an embodiment of a circuit of the pair of hearing protection devices.

FIG. 3 is a block diagram illustrating an embodiment of a circuit 304 of hearing protection devices 102. Circuit 304 includes a first hearing circuit 304A representing an embodiment of first hearing circuit 104A and a second hearing circuit 304B representing an embodiment of second hearing circuit 104B.

First hearing circuit 104A includes a microphone 330A, a communication circuit 332A, a processing circuit 334A, and a speaker 336A. Microphone 330A receives sounds from the environment of the shooter and produces a first acoustic signal representative of the received sounds. Communication circuit 332A communicates with portable device 110 and/or second hearing circuit 304B, including receiving signals from portable device 110 directly or through second hearing circuit 304B. Processing circuit 334A processes the sounds received by microphone 330A and/or an audio signal received by communication circuit 332A to produce a first output sound. Speaker 336A transmits the first output sound to the first ear canal of the shooter. In various embodiments, processing circuit 334A attenuates the gunshot sounds as received by microphone 330A and/or limits the sound level of the first output sound.

Second hearing circuit 104B includes a microphone 330B, a communication circuit 332B, a processing circuit 334B, and a speaker 336B. Microphone 330B receives sounds from the environment of the shooter and produces a second acoustic signal representative of the received sounds. Communication circuit 332B communicates with portable device 110 and/or first hearing circuit 304A, including receiving signals from portable device 110 directly or through first hearing circuit 304A. Processing circuit 334B processes the sounds received by microphone 330B and/or an audio signal received by communication circuit 332B to produce a second output sound. Speaker 336B transmits the second output sound to the second ear canal of the shooter. In various embodiments, processing circuit 334B attenuates the gunshot sounds as received by microphone 330B and/or limits the sound level of the first output sound.

Processing circuit 334A detects gunshots and produces the first detection information for each detected gunshot. In one embodiment, processing circuit 334A detects a first gunshot sound level being a peak sound level of the first acoustic signal. The peak sound level is associated with the gunshot indicated by the first acoustic signal produced by microphone 330A. Processing circuit 334A then detects a first gunshot time being a time of the detection of the first sound level (i.e., time of the peak sound level). In various embodiments, the first detection information including the first gunshot time and/or the first gunshot sound level.

Processing circuit 334B detects the same gunshots and produces the second detection information for each detected gunshot. In one embodiment, processing circuit 334B detects a second gunshot sound level being a peak sound level of the second acoustic signal. The peak sound level is associated with the gunshot indicated by the second acoustic signal produced by microphone 330B. Processing circuit 334B then detects a second gunshot time being a time of the detection of the second sound level (i.e., time of the peak sound level). In various embodiments, the second detection information includes the second gunshot time and/or the second gunshot sound level.

The first detection information and the second detection information allow for detection of the acoustic signature identifying the gunshot as being fired by the shooting using system 100. In various embodiments, the acoustic signature may include the time delay being the difference between the first gunshot time and the second gunshot time and/or the sound level difference being the difference between the first gunshot sound level and the second gunshot sound level. In one embodiment, first hearing circuit 304A transmits the first detection information to portable device 110, second hearing circuit 304B transmits the second detection information to portable device 110, and portable device 110 calculates the time delay and/or the sound level difference for detecting the acoustic signature. In another embodiment, first hearing circuit 304A transmits the first detection information to second hearing device 304A, and second hearing circuit 304B calculates the time delay and/or the sound level difference and transmits the calculated time delay and/or the calculated sound level difference to portable device 110 for portable device 110 to detect the acoustic signature.

Figure 4:
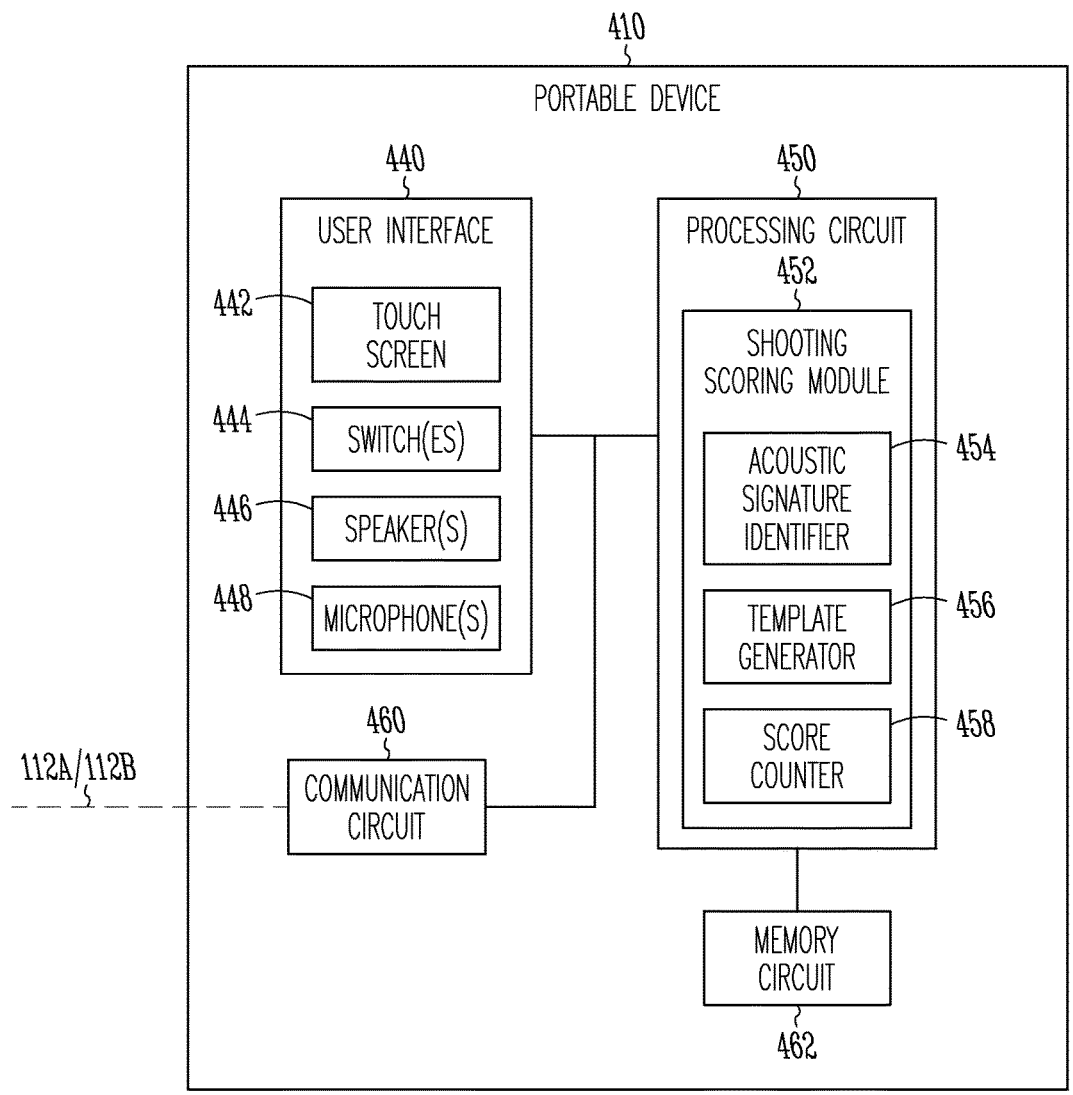
FIG. 4 is a block diagram illustrating an embodiment of a circuit of the portable device.

FIG. 4 is a block diagram illustrating an embodiment of a circuit of a portable device 410, which represents an embodiment of portable device 110. Portable device 410 includes a user interface 440, a communication circuit 460, a processing circuit 450, and a memory circuit 462.

User interface 440 includes a touch screen 442, one or more switches 444, one or more speakers 446, and one or more microphones 448. Touchscreen 442 may be configured to receive user commands, such as receiving commands from the shooter to start, pause, and stop scoring the shooting event, and displaying the shooting scores such as illustrated in FIG. 1 (portable device 110). One or more switches 444 allow for turning portable device 410 on and off, turning off a function of the device, and/or adjusting a function of the device. One or more speakers 446 emit various sounds including audio commands to the shooter if needed. One or more microphones 448 receive sounds from the shooter's environment, including voices of the shooter as voice commands if needed. In various embodiments, audio communication between portable device 410 and the shooter may be performed using one or more speakers 446 and one or more microphones 448 and/or using the microphones and speakers in hearing protection devices 102.

Communication circuit 460 allows portable device 410 to communicate with hearing protection devices 102 via wireless communication links 112A and/or 112B. In various embodiments, communication circuit 460 receives detection information including, or derived from, the first detection information and the second detection information.

Processing circuit 450 includes a shooting scoring module 452. In one embodiment, processing circuit 450 includes a mobile device such as a smartphone, and shooting scoring module 452 is implemented in the mobile device by installing an application software. Shooting scoring module 452 includes an acoustic signature identifier 454, a template generator 456, and a score counter 458.

Acoustic signature identifier 454 identifies the acoustic signature using the first detection information and the second detection information and a template signature. In various embodiments, the template signature is an acoustic signature characterizing a gunshot known to be fired by a specific individual shooter using a specific gun or a specific type of gun. This allows for identification of a detected gunshot as being fired by the specific individual shooter. In various embodiments, the acoustic signature includes the time delay being the difference between to first gunshot time and the second gunshot time, the sound level difference being the difference between the first gunshot sound level and the second gunshot sound level, or both of the time delay and the sound level difference, depending on whether each of these parameters is detectable in practice, and discussed above. In one embodiment, the acoustic signature identifier 454 receives the acoustic signature including the time delay and/or the sound level difference calculated by hearing protection device 102 and transmitted to portable device 410. In another embodiment, acoustic signature identifier 454 receives the first detection information and the second detection information from hearing protection device 102 and calculates the acoustic signature including the time delay and/or the sound level difference. In various embodiments, acoustic signature identifier 454 identifies a gunshot as being fired by the shooter when the acoustic signature matches the template signature.

Template generator 456 generates the template signature specific to the shooter and his or her gun and stores that template signature in memory device 462 for use by acoustic signature identifier 454. Because the template signature may have to be different for each shooting event, portable device 410 prompts the shooter to perform a calibration process upon activation of shooting scoring module 452. In one embodiment, template generator 456 produces a calibration tone prompting the shooter to fire one or more test gunshots. The calibration tone may be delivered to the shooter using one or more speakers 446 or using one or more speakers of hearing protection device 102. Template generator 456 produces the template signature using first detection information characterizing the one or more test gunshots as detected by first ear device 102A and second detection information characterizing the one or more test gunshots as detected by second ear device 102B. The template signature includes the same parameters as the acoustic signature to be identified by acoustic signature identifier 454, i.e., the time delay and/or the sound level difference. In one embodiment, template generator 456 produces the calibration tone to prompt the shooter to fire a plurality of test gunshots, such as 3 gunshots. The time delay is calculated as an average of the time delays calculated for two or more gunshots of the plurality of test gunshots. The sound level difference is calculated as an average of the sound level differences calculated for two or more gunshots of the plurality of test gunshots. Once generated, the template signature is stored in memory circuit 462.

Score counter 458 produces a scoring tone in response to an identification of the acoustic signature as being associated with a gunshot fired by the shooter. The scoring tone may be delivered to the shooter using one or more speakers 446 or using one or more speakers of hearing protection device 102. Score counter 458 times a detection period starting upon the delivery of the scoring tone, and detects a response command from the shooter during the detection period. The response command is a voice command and may be detected using one or more microphones 448 or using one or more microphones of hearing protection device 102. In one embodiment, the response command may be "hit" or "miss". The scoring tone prompts the shooter to say "hit" or "miss" as soon as the result of the gunshot is seen. In various embodiments, score counter 458 counts the number of hits, the number of misses, and/or the number of total shots. In one embodiment, score counter 458 counts the number of hits, the number of misses, and the number of total shots. In other embodiments, score counter 458 counts at least two of the number of hits, the number of misses, and the number of total shots. In various embodiments, score counter 458 counts scores derived from the number of hits, the number of misses, and/or the number of total shots.

Figure 5:
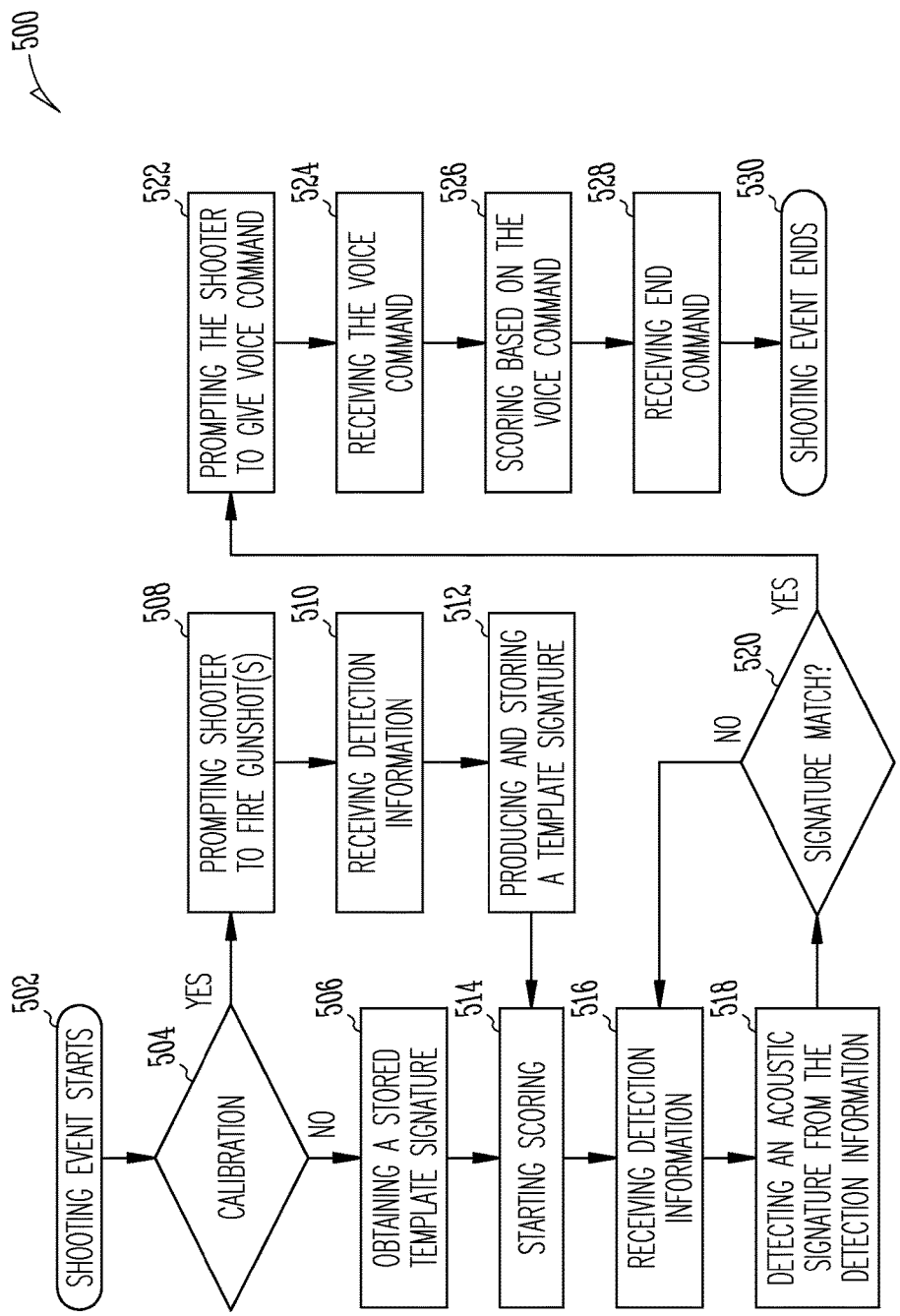
FIG. 5 is a flow chart illustrating an embodiment of a method for scoring a shooting event using a pair of hearing protection devices and a portable device.

FIG. 5 is a flow chart illustrating an embodiment of a method 500 for scoring a shooting event using hearing protection devices worn by a shooter and a portable device used by the shooter. In one embodiment, method 500 is performed using system 100. For example, portable device 110 or 410 is configured to perform method 500, together with a pair of hearing protection devices such as hearing protection devices 102. In one embodiment, the portable device is a mobile device such as a smartphone, and a shooting scoring application is installed in the mobile device to perform method 500.

At 502, a shooting event starts. Examples of the shooting event include traditional clay pigeon shooting events such as trap shooting, skeet shooting, and sporting clays, as well as other shooting sports such as biathlon and 3-gun shooting events.

At 504, the shooter may optionally be asked if a calibration is needed. The calibration is a process that determines the template signature for scoring the shooting event. The template signature includes parameters used in the acoustic signature used in the shooting event for identifying each gunshot fired by the shooter. In various embodiments, the acoustic signature includes the time delay being the difference between to first gunshot time and the second gunshot time, the sound level difference being the difference between the first gunshot sound level and the second gunshot sound level, or both of the time delay and the sound level difference, depending on whether each of these parameters is detectable in practice, and discussed above. If the shooter answers no, a stored template signature is obtained for use during the shooting event at 506. The stored template signature may be a template signature previously created for the same shooter using the same gun. If the shooter answers yes, he or she is prompted to fire one or more test gunshots at 508. At 510, detection information regarding the one or more test gunshots as detected by each of the hearing protection devices is received. At 512, a template signature is produced using the detection information and stored. In one embodiment, the shooter is prompted to fire a plurality of test gunshots, such as 3 gunshots. The time delay is calculated as an average of the time delays calculated for two or more gunshots of the plurality of test gunshots. The sound level difference is calculated as an average of the sound level differences calculated for two or more gunshots of the plurality of test gunshots. In one embodiment, method 500 does not include steps 504 and 506, and the calibration of steps 508, 510, and 512 are mandatory.

At 514, the template signature is obtained and ready for use, and the scoring for the shooting events starts. At 516, detection information characterizing each gunshot detected by the hearing protection devices is received. At 518, an acoustic signature is detected from the received detection information. If the detected acoustic signature does not match the template signature at 520, the gunshot is identified as a gunshot from another shooter and therefore not to be scored. If the detected acoustic signature matches the template signature at 520, the gunshot is identified as a gunshot fired by the shooter and therefore to be scored. At 522, upon identification of the gunshot as being fired by the shooter, the shooter is prompted to give a voice command. In one embodiment, the voice command can be either "hit" or "miss". At 524, the voice command is received. At 526, the score is updated based on the voice command. In various embodiments, the number of hits, the number of misses, and/or the number of total shots are counted. In one embodiment, all of the number of hits, the number of misses, and the number of total shots are counted and displayed on a screen of the portable device. In other embodiments, at least two of the number of hits, the number of misses, and the number of total shots are counted and displayed on the screen of the portable device. In various embodiments, scores derived from the number of hits, the number of misses, and/or the number of total shots may be tracked and displayed on the screen of the portable device.

At 528, an end command is received to stop the scoring. In various embodiments, the end command may be entered by the shooter or generated automatically when a predetermined total number of gunshots is reached.

At 530, the shooting event ends. In one embodiment, the score may be reset and/or adjusted by the shooter at any time between the start of the scoring at 514 and receipt of the end command at 528, such as to correct a scoring error observed by the shooter.

It is understood that the hearing circuits referenced in this patent application (such as first hearing circuit 104A or 304A and second hearing circuit 104B or 304B) include a processor (such as a processor implementing processing circuit 334A or 334B). The processor may be a digital signal processor (DSP), microprocessor, microcontroller, or other digital logic. The processing of signals referenced in this application can be performed using the processor. Processing may be done in the digital domain, the analog domain, or combinations thereof. Processing may be done using subband processing techniques. Processing may be done with frequency domain or time domain approaches. For simplicity, in some examples blocks used to perform frequency synthesis, frequency analysis, analog-to-digital conversion, amplification, and certain types of filtering and processing may be omitted for brevity. In various embodiments the processor is adapted to perform instructions stored in memory which may or may not be explicitly shown. In various embodiments, instructions are performed by the processor to perform a number of signal processing tasks. In such embodiments, analog components are in communication with the processor to perform signal tasks, such as microphone reception, or receiver sound embodiments (i.e., in applications where such transducers are used). In various embodiments, realizations of the block diagrams, circuits, and processes set forth herein may occur without departing from the scope of the present subject matter.

The present subject matter is demonstrated for hearing protection devices, including but not limited to earbuds, earmuffs, or ear plugs, that protect the wearer's hearing from loud noises while allowing for listening of environmental sounds and/or steamed audio such as music or phone calls. In some embodiments, the pair of hearing protection devices is implemented as a pair of hearing assistance devices housed in cases configured to protect the wearer from the loud noises. The present subject matter is demonstrated for hearing assistance devices, including hearing aids, including but not limited to, behind-the-ear (BTE), in-the-ear (ITE), in-the-canal (ITC), receiver-in-canal (RIC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user, including but not limited to receiver-in-canal (RIC) or receiver-in-the-ear (RITE) designs. The present subject matter can also be used with hearing assistance devices generally, such as cochlear implant type hearing devices used with external hearing protection devices such as earbuds, earplugs, and earmuffs. It is understood that other hearing assistance devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A system for scoring a shooting event for a shooter having a first ear and a second ear, the system comprising:
a pair of hearing protection devices configured to protect hearing of the shooter from injurious sounds, the pair of hearing protection devices including:
a first ear device configured to be worn in or over the first ear, to detect gunshots, and to produce first detection information characterizing each of the gunshots as detected by the first ear device; and
a second ear device configured to be worn in or over the second ear, to detect the gunshots, and to produce second detection information characterizing each of the gunshots as detected by the second ear device; and
a portable device configured to be communicatively coupled to the pair of hearing protection devices, detect an acoustic signature using the first detection information and the second detection information, and identify each gunshot fired by the shooter from the gunshots detected by the first and second ear devices using the detected acoustic signature and a template signature, the template signature allowing for the identification of each gunshot fired by the shooter based on lengths of sound paths through which a sound of the gunshot being identified travels to the first ear device and the second ear device.

2. The system of claim 1, wherein the portable device is further configured to receive a voice command from the shooter following the identification of the each gunshot fired by the shooter and score the each gunshot according to the voice command.

3. The system of claim 2, wherein the shooting scoring module comprises a signature identifier configured to identify a time delay as the acoustic signature, the time delay being a difference between a time of the detection of the each of the gunshots by the first ear device and a time of the detection of the each of the gunshots by the second ear device.

4. The system of claim 2, wherein the shooting scoring module comprises a signature identifier configured to identify a sound level difference as the acoustic signature, the sound level difference being a difference between a sound level of the each of the gunshots as detected by the first ear device and a sound level of the each of the gunshots as detected by the second ear device.

5. The system of claim 2, wherein the processing circuit comprises a score counter configured to produce a scoring tone to be delivered to the shooter using the pair of hearing protective devices in response to the identification of the each gunshot fired by the shooter, time a detection period starting upon the delivery of the scoring tone, and detect the voice command from the shooter during the detection period.

6. The system of claim 5, wherein the processing circuit comprises a template generator configured to prompt the shooter to fire one or more test gunshots, and produce the template signature using the first detection information and the second detection information associated with the one or more test gunshots.

7. The system of claim 1, wherein the portable device is configured to be communicatively coupled to the pair of hearing protection devices via a wireless link.

8. The system of claim 7, wherein the pair of hearing protective devices comprises a pair of earbuds, a pair of earmuffs, or a pair of earplugs.

9. The system of claim 8, wherein the portable device comprises a smartphone, a laptop computer, a tablet computer, or a personal digital assistance device.

10. A method for scoring a shooting event for a shooter wearing a pair of hearing protection devices configured to protect hearing of the shooter from injurious sounds, the method comprising:
receiving detection information characterizing each gunshot of gunshots detected by the pair of hearing protective devices;
detecting an acoustic signature from the received detection information, the acoustic signature including one or more parameters allowing for identification of each gunshot fired by the shooter from the gunshots detected by the pair of hearing protective devices;
determining whether the detected acoustic signature for the each gunshot matches a template signature; and
identifying the each gunshot as being fired by the shooter in response to the determination that the detected acoustic signature for the each gunshot matches the template signature,
wherein the template signature allows for the identification of the each gunshot as being fired by the shooter based on lengths of sound paths each being a path through which a sound of the each gunshot travels to one device of the pair of hearing protective devices.

11. The method of claim 10, further comprising:
prompting the shooter to give a voice command; and
counting a score based on the voice command.

12. The method of claim 11, wherein the one or more parameters comprise a time delay between the each gunshot as detected by a first ear device of the pair of hearing protection devices and the each gunshot as detected by a second ear device of the pair of hearing protection devices.

13. The method of claim 11, wherein the one or more parameters comprise a sound level difference between a sound level of the each gunshot as detected by a first ear device of the pair of hearing protection devices and a sound level of the each gunshot as detected by a second ear device of the pair of hearing protection devices.

14. The method of claim 13, wherein the one or more parameters comprise a time delay and the sound level difference, the time delay being a difference between a time of the each gunshot as detected by a first ear device of the pair of hearing protection devices and a time of the each gunshot as detected by a second ear device of the pair of hearing protection devices.

15. The method of claim 11, wherein counting the score comprises counting at least two of a number of hits, a number of misses, and a number of total shots.

16. The method of claim 11, further comprising determining the template signature for the shooting event using a calibration process including:
prompting the shooter to fire one or more test gunshots;
receiving the detection information characterizing the one or more test gunshots; and
producing the template signature using the detection information characterizing the one or more test gunshots.

17. A portable device for scoring a shooting event for a shooter wearing a pair of hearing protection devices including first and second ear devices configured to protect hearing of the shooter from injurious sounds, the portable device comprising:

a communication circuit configured to receive detection information regarding gunshots detected by the pair of hearing protection devices from the pair of hearing protection devices via a wireless link, the detection information including or derived from first detection information characterizing each of gunshots as detected by the first ear device and second detection information characterizing the each of the gunshots as detected by the second ear device; and a processing circuit configured to identify an acoustic signature using the detection information and identify each gunshot fired by the shooter from the gunshots detected by the pair of hearing protection devices in response to the identified acoustic signature matching a template signature, the template signature allowing for the identification of each gunshot fired b the shooter based on lengths of sound paths through which a sound of the gunshot being identified travels to the first and second ear devices.

18. The portable device of claim 17, wherein the processing circuit is further configured to produce a scoring tone to be delivered to the shooter using the pair of hearing protection devices in response to the identification of the each gunshot fired by the shooter, time a detection period, detect a response command from the shooter during the detection period, and count a score based on the response command.

19. The portable device of claim 18, wherein the processing circuit is further configured to identify a time delay as the acoustic signature, the time delay being a difference between a time of the detection of the each of the gunshots by the first ear device and a time of the detection of the each of the gunshots by the second ear device.

20. The portable device of claim 18, wherein the processing circuit is further configured to identify a sound level difference as the acoustic signature, the sound level difference being a difference between a sound level of the each of the gunshots as detected by the first ear device and a sound level of the each of the gunshots as detected by the second ear device.

21. The portable device of claim 17, wherein the processing circuit is further configured to prompt the shooter to fire one or more test gunshots and produce the template signature using the detection information associated with the one or more gunshots.

* * * * *